United States Patent [19]

Maki

[11] Patent Number: 4,474,885

[45] Date of Patent: Oct. 2, 1984

[54] METHOD OF ANALYZING FUEL OIL FOR CATALYST COMPONENT

[75] Inventor: Hiroya Maki, Nagasaki, Japan

[73] Assignee: Mitsubishi Jukogyo Kabushiki Kaisha, Japan

[21] Appl. No.: 398,628

[22] Filed: Jul. 15, 1982

Related U.S. Application Data

[63] Continuation of Ser. No. 225,537, Jan. 16, 1981, abandoned.

[51] Int. Cl.³ .............................................. G01N 33/22
[52] U.S. Cl. ........................................ 436/37; 436/72; 436/175
[58] Field of Search ..................... 23/230 HC, 230 M; 436/37, 72, 175

[56] References Cited

U.S. PATENT DOCUMENTS 4,333,908  6/1982  Maki et al. .................... 436/72 X

FOREIGN PATENT DOCUMENTS 55-104755  8/1980  Japan ................................ 436/72
55-106356  8/1980  Japan ................................ 436/37

*Primary Examiner*—Kenneth M. Schor
*Attorney, Agent, or Firm*—McGlew and Tuttle

[57] ABSTRACT

A method of analyzing fuel oil for a catalyst component which comprises dissolving a sample amount of the oil in an organic solvent, filtering the oil solution, bringing the filtration residue into contact with hydrofluoric acid to dissolve the silicon contained in the residue into the acid, and then subjecting the silicon solution to colorimetric analysis for the determination of the Si ion content.

5 Claims, No Drawings

METHOD OF ANALYZING FUEL OIL FOR CATALYST COMPONENT

This is a continuation of application Ser. No. 225,537 filed Jan. 16, 1981, now abandoned.

This invention relates to a simple and speedy method for field analysis of fuel oil for a catalyst component.

Fuel oil for marine engines has commonly been a mixture of light gas oil and long and short residuums from atmospheric and vacuum distillations, respectively. However, in order to meet growing demand for light oil and save the fuel cost, there is an increasing tendency in the art to squeeze out an additional percentage of light gas oil from the long and short residuums by thermal or catalytic cracking or other technique and then mix the thickened residue with light gas oil or the like as fuel for marine engines. The mixed fuel thus formed is high in specific gravity and viscosity, with by far the greater carbon residue than the ordinary heavy fuel oil C.

The residue after the extraction of light gas oil by catalytic cracking is generally known as fluid catalytic cracking (FCC) oil. It contains hard microspheriods of a silica-alumina catalyst, ranging in particle size from 5 to 80$\mu$, as the catalyst for catalytic cracking. When a fuel oil containing such hard particles of the silica-alumina catalyst is employed as fuel, for example, for diesel engines, unusual wear of piston rings and cylinder liners will understandably result. There are instances in which fuels incorporating FCC oils with Si contents of 300 to 3000 ppm caused rapid wear of the rings and liners in diesel engines.

If this premature wear is to be avoided, it will be necessary to know if any FCC oil is incorporated in the fuel and, if so, remove it or reject the fuel oil. Nevertheless, no technique has been established yet for simply and rapidly detecting by field analysis the presence of the silica-alumina catalyst in the FCC oil as fuel. A conventional practice has been to ash the questionable fuel oil once, dissolve the ash in a solvent, and subject the resulting solution to a colorimetric analysis for silica. The fuel oil ashing is conducted in conformity with the procedure of Japanese Industrial Standards K-2272 (Testing Method for Determination of Ash Contents in Crude Oils and Petroleum Products). The procedure consists in gradually carbonizing the fuel by weak heating until the oil ceases to give off any more volatile matter, and then reducing the resultant material to ash by heating at about 800° C. Thus, complete ashing takes about two days, or too much time to meet field requirements.

The present invention has for its object to provide a method for field analysis to determine the catalyst component content in fuel oil in a simple and quick way, whereby the fuel oil supplied to a ship at any port of call for her engines can be conveniently and promptly analyzed to see if it contains the FCC oil and avoid the use of any fuel oil containing the same and thereby prevent troubles of the diesel engines and the like.

To attain this end, the invention comprises dissolving a sample amount of fuel oil in an organic solvent, filtering the solution and separating out the residue, that is, the silica-alumina catalyst, dissolving its main component silica into hydrofluoric acid, and then subjecting the resulting solution to colorimetric determination of its Si ion content. Without the need of ashing the residue, the method of the invention is advantageous over the conventional technique in that it permits simpler and quicker determination of the silica content and easier detection of the FCC oil present in the fuel. The method is, therefore, effectively applicable to the evaluation of a given fuel (usually fuel oil C), as to its adequacy or inadequacy for given thermal engines, such as diesels or boilers.

The above and other objects, features, and advantages of the invention will become more apparent from the following detailed description.

The method of the invention is practiced in the manner now to be described. First, not more than five grams of a fuel oil is sampled into a beaker, and 100 ml of at least one organic solvent, for example, benzene, toluene, xylene, hexane, petroleum benzine, trichloroethylene, or tetrachloroethylene, is added to the oil. The beaker is placed in an ultrasonic cleaner for 10–15 minutes with stirring (or into a water bath at 60°–70° C. for 30 minutes with stirring from time to time) until the fuel oil and the solvent are thoroughly mixed up in solution. The time for dissolution can be further shortened by increasing the temperature of the water bath in the ultrasonic cleaner to about 60°–70° C.

The temperature range of about 60°–70° C. is chosen because it is below the boiling points of solvents; with some solvents, the use of higher temperatures can be dangerous. The boiling points of the above-mentioned solvents, for example, are: 80° C. for benzene, 111° C. for toluene, 144° C. for xylene, 69° C. for hexane, 80°–100 C. for petroleum benzine, 86.6° C. for trichloroethylene, and 121.2° C. for tetrachloroethylene.

Next, the solution thus prepared is passed through a filter using a filter medium of ethylene tetrafluoride membrane (for example, the one made by Sumitomo Electric Industries, Ltd. and marketed under the trade designation of "Fluoropore filter") to separate out the residue from the fuel oil. The residue, in turn, is brought into contact with 0.2–1 wt% of hydrofluoric acid to dissolve silica, the principal component of the silica-alumina catalyst in the residue. A suitable amount of the solution so obtained is sampled and, in the vicinity of pH 1.5, ammonium molybdate is added to develop the color of molybdenum yellow. By the addition of 1-amino-2-naphthol-4-sulfonic acid (hereinafter called "ANSA") as a reducing agent, it is reduced to molybdenum blue. Then, the intensity of the resulting blue is compared with that of the standard in accordance with the so-called molybdenum blue method for colorimetric determination of Si ions. On the basis of an analytical curve drawn in advance, the Si quantity is measured.

In the foregoing description the silica content is determined by analysis as representing the silica-alumina catalyst, because the catalyst available for the model procedure was of a composition largely dominated by silica, viz., 68.4 wt% $SiO_2$ versus 9.6 wt% $Al_2O_3$.

By way of information, a typical composition of the silica-alumina catalyst [according to "HANNOBETSU JITSUYO SHOKUBAI" (Practical Catalysts Classified by Types of Reactions), Kagaku-Kogyo-sha, publsd. Dec. 25, 1970, pp. 640–641] is as given in Table 1.

TABLE 1

| Component | SiO$_2$ | Al$_2$O$_3$ | MgO | Fe$_2$O$_3$ | CaO | TiO$_2$ | SO$_2$ | Ignition loss |
|---|---|---|---|---|---|---|---|---|
| Weight % | 66.6 | 15.4 | 4.3 | 2.3 | 0.4 | 3.0 | 3.0 | 3.8 |

As can be seen from the table, silica accounts for nearly 70% of the total weight of the typical silica-alumina catalyst.

The method of the invention has the following advantages:

(1) Since a fuel oil sample is dissolved in an organic solvent and the residue is separated out by filtration, the time required for the residue extraction is remarkably shortened from the length of time usually needed by the conventional ashing treatment. To be more exact, this method takes only one hour for the procedure whereas the prior art method requires two full days. Moreover, because the object of colorimetric analysis is silica, the chief constituent of the silica-alumina catalyst, simpler and speedier field analysis is made possible than the ordinary method that involves ashing.

(2) Mere analysis of fuel oil for SiO$_2$ gives an indication of whether the particular fuel contains the FCC oil, that is, whether it is unsuitable for use as fuel or not.

(3) The presence of the FCC oil being detectable, it is possible for a ship's crew or the like to reject the fuel oil containing it so as to prevent troubles of their diesel engines or the like.

The invention is illustrated by examples as follows:

(1) In each example, a two-gram sample of a test fuel oil is placed into a 200-ml beaker, 100 ml of benzene is added, and the both are mixed with stirring in an ultrasonic cleaner for 15 minutes. The resulting solution is passed through a filter using the above-mentioned Fluoropore filter medium (0.65$\mu$ in mesh size). The beaker and the filter are washed with benzene in a washing bottle until the filtrate becomes clear.

(2) From the filter the Fluoropore filter medium is taken out and dried at room temperature.

(3) Next, 10 ml of a 0.25 wt% hydrofluoric acid solution is introduced into a 50-ml beaker of polyethylene with a polyethylene pipette. Inside this beaker the Fluoropore filter medium is kept immersed, with its filtration face in contact with the hydrofluoric acid solution, with intermittent agitation for 15 minutes.

(4) From the polyethylene beaker 5 ml of the liquid is transferred to a 100-ml polyethylene cylinder with a polyethylene pipette. Following the addition of 2 ml of a 0.25 mol/l Al$_2$(SO$_4$)$_3$ solution, the mixed solution is diluted with ion exchange water to a total volume of 50 ml. The Al$_2$(SO$_4$)$_3$ solution is added in order to provide a shelter from the effects of F ions at the time of colorimetric determination.

(5) One milliliter of an H$_2$SO$_4$ [1 (H$_2$SO$_4$)+4 (H$_2$O)] solution is added to the solution to adjust its pH value. After the addition of 5 ml of a 10 wt% ammonium molybdate solution, the mixture is stirred and allowed to stand for 5 minutes so as to develop the color of molybdenum yellow. With the further addition of 2 ml of a 20 wt% citric acid solution and then 4 ml of the afore-mentioned ANSA solution, the mixed solution is reduced to molybdenum blue and is tested by colorimetry for 15 minutes.

(6) Standard Si solutions (10 $\mu$g Si/ml) are prepared stepwise to draw analytical curves for the steps (3) to (5) beforehand and, on the basis of those curves, the Si content is determined.

The above procedure was repeated with all of test fuel oils in examples for the colorimetric determination of their Si contents. The results, as compared with those by the conventional ashing method, are shown in Table 2.

In Table 2 the fuel oil tested, No. 1, is the oil from thermal cracking, No. 2 is an FCC-oil-containing fuel oil, and No. 10 is heavy fuel oil C. As can be seen from the table, there are clear distinctions between the oils in the Si content.

Other test oils are from unknown processes, but it is very likely that No. 8 contains an FCC oil.

Reproducibility of the method is relatively high. As indicated by the repeated runs of analysis for Nos. 2 and 8, the determined values are approximately equal to those obtained by the ashing method of the prior art. These testify to the fact that the method of the invention is effective as a simple and speedy technique for field analysis of fuel oil for its Si content and that it is also a simplified method for detecting and identifying FCC-oil-containing fuel oil.

TABLE 2

| No. of runs for analysis | Analytical results (for Si) (in ppm) Fuel oil analyzed | | | | | | | | | |
|---|---|---|---|---|---|---|---|---|---|---|
| | No. 1 | No. 2 | No. 3 | No. 4 | No. 5 | No. 6 | No. 7 | No. 8 | No. 9 | No. 10 |
| 1 | 1.25 | 40.2 | 7.1 | 5.0 | 2.9 | 3.9 | 5.0 | 71.6 | 0 | 4.2 |
| 2 | | 42.3 | 6.8 | 4.9 | | | | 67.4 | | 3.6 |
| 3 | | 36.3 | 7.5 | 5.0 | | | | 51.0 | | 4.0 |
| 4 | | 47.9 | 8.1 | 5.7 | | | | 55.6 | | 3.8 |
| 5 | | 47.7 | 8.7 | 4.8 | | | | 53.6 | | 3.6 |
| 6 | | 45.8 | | 4.7 | | | | 67.3 | | 4.3 |
| Average | | 43.47 | 7.64 | 5.02 | | | | 61.08 | | 3.92 |
| Ashing method | — | 44.0 | — | — | — | — | — | 56.8 | — | — |

What is claimed is:

1. Method of analyzing fuel oil for a catalyst component which comprises the steps of:
(a) thoroughly mixing the fuel oil and an organic solvent with stirring in an ultrasonic cleaner zone sufficiently for dissolving the oil in the organic solvent to provide an oil-containing solution,
(b) filtering the oil containing solution to provide a filtration residue, (c) bringing the filtration residue into contact with hydrofluoric acid to dissolve the silicon contained in said residue into said acid and thereby form a silicon containing solution, and then (d) subjecting the silicon containing solution to colorimetric analysis for the determination of the Si ion content therein.

2. Method of claim 1 wherein step (a) is carried out at a temperature below the boiling point of said organic solvent.

3. Method of claim 1 wherein step (a) is carried out in said zone for 10 to 15 minutes.

4. Method of claim 1 wherein the silicon containing solution from step (c) is treated with an aqueous sheltering agent prior to subjecting said silicon containing solution to step (d), whereby to provide a shelter from the effects of F ions, derived from the hydrofluoric acid, at the time of said colorimetric analysis.

5. Method of claim 4, wherein said sheltering agent is aqueous aluminium sulfate.

* * * * *